United States Patent [19]
Gelfand et al.

[11] Patent Number: 5,665,551
[45] Date of Patent: Sep. 9, 1997

[54] PURIFIED NUCLEIC ACID ENCODING A THERMOSTABLE PYROPHOSPHATASE

[75] Inventors: David Harrow Gelfand, Oakland; Alice Ming Wang, Lafayette, both of Calif.

[73] Assignee: Roche Molecular Systems, Inc., Branchburg, N.J.

[21] Appl. No.: 528,384

[22] Filed: Sep. 13, 1995

[51] Int. Cl.$^6$ .............................. C12N 9/14; C12N 15/55
[52] U.S. Cl. ...................... 435/6; 435/195; 435/320.1; 435/325; 435/419; 435/252.3; 536/23.2
[58] Field of Search .......................... 435/195, 320.1, 435/240.1, 240.2, 240.4, 252.3, 252.33, 325, 419, 6; 536/23.2

[56] References Cited

U.S. PATENT DOCUMENTS 5,498,523  3/1996  Tabor et al. ................................ 435/6

FOREIGN PATENT DOCUMENTS 9012111  10/1990  WIPO.
9405797   3/1994  WIPO.

OTHER PUBLICATIONS

Hohne et al., 1988, "Kinetic Characterization of a Thermostable Inorganic Pyrophosphatase from Thermus thermophilus" Biomed. Biochim. Acta. 47(12):941–947.

Kolakowski et al., 1988, "Cloning, Molecular Characterization and Chromosome Localization of the Inorganic Pyrophosphatase (PPA) Gene From S. Cerevisiae" Nucleic Acids Research 16(22):10441–10452.

Lahti et al., Dec., 1988, "Cloning and Characterization of the Gene Encoding Inorganic Pyrophosphatase of *Escherichia coli* K–12" J. Bacteriology 170(12):5901–5907.

Tabor and Richardson, 1990, "DNA Sequence Analysis With a Modified Bacteriophage T7 DNA Polymerase" J. Biological Chemistry 265(14):8322–8328.

Richter and Schafer, 1992, "Purification and Enzymic Characterization of the Cytoplasmic Pyrophosphatase from the Thermoacidophilic Archaebacterium Thermoplasma Acidophilum" Eur. J. Biochem. 209:343–349.

Richter and Schafer, 1992, "Cloning and Sequencing of the Gene for the Cytoplasmic Inorganic Pyrophosphatase from the Thermoacidophilic Archaebacterium Thermoplasma Acidophilum" Eur. J. Biochem. 209:351–355.

Yang and Wensel, 1992, "Molecular Cloning and Functional Expression of cDNA Encoding a Mammalian Inorganic Pyrophosphatase" J. Biological Chemistry 267(34):24641–24647.

Obmolova et al., 1993, "Purification, Crystallization and Preliminary X–ray Analysis of Inorganic Pyrophosphatase from Thermus Thermophilus" J. Mol. Biol. 232:312–313.

Teplyakov et al., 1994, "Crystal Structure of Inorganic Pyrophosphatase From Thermus Thermophilus" Protein Science 3:1098–1107.

Boyer, P.D., The Enzymes, 3rd ed., New York, Academic Press, 1971, Chapter 20, entitled "Inorganic Pyrophosphatase of *Escherichia coli*".

Sambrook et al. "Molecular Cloning: A Laboratory Manual", 1989, Cold Spring Harbor Press, pp. 11.3–11.19.

*Primary Examiner*—Keith D. Hendricks
*Attorney, Agent, or Firm*—George W. Johnston; Stacey R. Sias; Douglas A. Petry

[57] ABSTRACT

Purified DNA sequences that encode a thermostable pyrophosphatase are provided. The purified DNA is obtained using a DNA probe consisting of SEQ ID NO: 1. Also provided are methods for producing thermostable pyrophosphatase.

7 Claims, No Drawings

PURIFIED NUCLEIC ACID ENCODING A THERMOSTABLE PYROPHOSPHATASE

FIELD OF THE INVENTION

The present invention relates to the in vitro synthesis of a thermostable pyrophosphatase. Thermostable pyrophosphatases are useful in many recombinant DNA techniques, especially nucleic acid sequencing and nucleic acid amplification by the polymerase chain reaction (PCR).

BACKGROUND ART

Pyrophosphate is a common product of biosynthetic reactions. Inorganic pyrophosphatase (PPase), also known as pyrophosphate phosphohydrolase, catalyzes hydrolysis of inorganic pyrophosphate (PPi) to two molecules of orthophosphate. PPase plays an vital role in RNA and DNA synthesis in vivo. By cleaving PPi, the enzyme shifts the overall equilibrium in favor of synthesis.

DNA polymerases catalyze the template-dependent incorporation of a deoxynucleotide onto the 3' hydroxyl terminus of a primer, with the concomitant release of inorganic pyrophosphatase (PPi). This polymerization reaction is reversible. DNA polymerases also catalyze the reverse reaction, pyrophosphorolysis, which is the degradation of DNA in the presence of PPi. The reaction is summarized below:

In vitro nucleic acid amplification methods, such as the polymerase chain reaction (PCR), require DNA polymerization. PCR is described in U.S. Pat. Nos. 4,683,195; 4,683,202; and 4,965,188, each incorporated herein by reference. In each cycle of a PCR amplification, a double-stranded target sequence is denatured, primers are annealed to each strand of the denatured target, and the primers are extended by the action of a DNA polymerase. The process is repeated typically between 25 and 40 times. Initial amplification conditions are chosen which favor the forward (polymerization) reaction (high dNTP concentrations, low pyrophosphate concentration). However, the amplification reaction results in an accumulation of pyrophosphate which increases the rate of the reverse reaction (pyrophosphorolysis), thereby decreasing the overall efficiency of the amplification reaction.

Similarly, pyrophosphorolysis can be detrimental to DNA sequencing reactions. Accuracy in DNA sequencing reactions depends on precise band position, a decrease in size of only one nucleotide can result in gel artifacts such as diffuse or missing bands. Pyrophosphorolysis results in the removal of bases from the 3' end of the primer extension product. Furthermore, removal of the terminal ddNMP from a ddNMP-terminated fragment allows subsequent extension.

Thus, in both amplification and sequencing reactions, it is desirable to minimize the pyrophosphorolysis reaction. The addition of PPase to the reaction shifts the overall equilibrium in favor of synthesis by cleaving PPi. The use of PPase to improve sequencing reactions is described in Tabor and Richardson, 1990, *J. Biol. Chem.* 265(14):8322–8328; and in PCT Patent Publication No. WO 90/12111; both incorporated herein by reference. The use of PPase in to improve DNA synthesis by a DNA polymerase is described in PCT Patent Publication No. WO 94/05797, incorporated herein by reference.

Native PPase protein has been isolated from *Thermus thermophilus* and *Thermus ruber* cells (WO 94/05797). Purification of native protein is time consuming and labor intensive.

SUMMARY OF THE INVENTION

The present invention provides purified DNAs which encode a thermostable pyrophosphatase.

One aspect of the invention relates the purified DNA which encodes a thermostable pyrophosphatase (PPase) from a species of the genus Thermus, recombinant DNA vectors which contain the DNA, and host cells transformed with the recombinant DNA vectors. DNA encoding PPase from species of the genus Thermus have substantial homology, and can be identified and isolated using a DNA consisting of SEQ ID NO: 1 as a probe. Once identified and isolated, the encoding DNA can be used to construct expression vectors in order to produce commercial quantities of the thermostable PPase.

In a preferred embodiment of the invention, the purified DNA is SEQ ID NO: 1.

Another aspect of the invention relates to methods for preparing a thermostable pyrophosphatase using the purified DNA of the present invention. A recombinant expression vector is expressed in a host cell, and the expressed protein is purified from the host cell.

DETAILED DESCRIPTION OF THE INVENTION

The present invention provides DNA sequences and expression vectors that encode a thermostable pyrophosphatase (PPase). To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells are known to utilize promoters, polyadenylation signals, and enhancers.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length gene sequence or by any portion of the coding sequence so long as the enzymatic activity is retained.

The term "operably linked" refers to the positioning of the coding sequence, such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing the thermostable PPase refers to a collection of materials which includes the PPase but which can also include other proteins. If the PPase is derived from recombinant host cells, the other proteins will ordinarily be those associated with the host. Where the host is bacterial, the contaminating proteins will, of course, be bacterial proteins.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68: 109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3): 165–187, incorporated herein by reference.

The term "primer" as used herein refers to an oligonucleotide which is capable of acting as a point of initiation of synthesis when placed under conditions in which primer extension is initiated. Synthesis of a primer extension product which is complementary to a nucleic acid strand is initiated in the presence of four different nucleoside triphosphates and a thermostable DNA polymerase in an appropriate buffer at a suitable temperature. A "buffer" includes cofactors (such as divalent metal ions) and salt (to provide the appropriate ionic strength), adjusted to the desired pH.

The terms "restriction endonucleases" and "restriction enzymes" refer to bacterial enzymes which cut double-stranded DNA at or near a specific nucleotide sequence.

The term "thermostable enzyme", as used herein, refers to an enzyme which is stable to heat and has an elevated temperature reaction optimum. The thermostable pyrophosphatase encoded by the nucleic acid sequence of the present invention catalyzes the cleavage of PPi optimally at a temperature between 60° and 90° C.

Conventional techniques of molecular biology and nucleic acid chemistry, which are within the skill of the art, are fully explained fully in the literature. See, for example, Sambrook et al., 1985, *Molecular Cloning—A Laboratory Manual*, Cold Spring Harbor Laboratory, Cold Spring Harbor, N.Y.; *Oligonucleotide Synthesis* (M. J. Gait, ed., 1984); *Nucleic Acid Hybridization* (B. D. Hames and S. J. Higgins, eds., 1984); and a series, *Methods in Enzymology* (Academic Press, Inc.), all of which are incorporated herein by reference. All patents, patent applications, and publications mentioned herein, both supra and infra, are incorporated herein by reference.

The present invention provides a DNA sequence which encodes a thermostable pyrophosphatase. The DNA sequences designated SEQ ID NO: 1, is shown below oriented 5' to 3'. By convention, the coding strand of the double-stranded DNA that is SEQ ID NO: 1 is shown; the sequence of the complementary non-coding strand is implicitly provided by reference to the sequence of the coding strand. It will be clear to one of skill in the art that as used herein, references to SEQ ID NO: 1, depending on the context, are meant to encompass either the double-stranded DNA or one (or either) of the constituent strands. For example, a single-stranded probe consisting of SEQ ID NO: 1 refers to the coding sequence shown below, or to the complementary non-coding sequence, whereas an expression clone comprising SEQ ID NO: 1 typically contains the double-stranded DNA.

| DNA Encoding a Thermostable Pyrophosphatase (SEQ ID NO: 1) | | | | |
|---|---|---|---|---|
| 1 ATGGCGAACC | TGAAGAGCCT | TCCCGTGGGC | GACAAGGCGC | CCGAGGTGGT |
| 51 CCACATGGTC | ATTGAGGTCC | CCCGCGGCTC | GGGCAACAAG | TACGAGTACG |
| 101 ACCCGGACCT | CGGGGCGATC | AAGCTGGACC | GGGTCCTGCC | GGGAGCCCAG |
| 151 TTCTACCCCG | GGGACTACGG | CTTCATCCCC | TCCACCCTGG | CCGAGGACGG |
| 201 GGACCCCTTG | GACGGCCTCG | TCCTCTCCAC | CTACCCCCTC | CTCCCCGGGG |
| 251 TGGTGGTGGA | GGTCCGGGTG | GTGGGCCTCC | TCCTCATGGA | GGACGAGAAG |
| 301 GGCGGGGATG | CCAAGGTCAT | CGGGGTGGTG | GCCGAGGACC | AGCGCCTGGA |
| 351 CCACATCCAG | GACATCGGGG | ACGTCCCCGA | GGGCGTGAAG | CAAGAGATCC |
| 401 AGCACTTCTT | TGAGACCTAC | AAGGCCCTCG | AGGCCAAGAA | GGGGAAGTGG |
| 451 GTCAAGGTCA | CGGGCTGGCG | GGACCGGAAG | GCGGCCTTGG | AGGAGGTCCG |
| 501 GGCCTGCATC | GCCCGCTACA | AGGGCTAG | | |

A DNA sequence that is SEQ ID NO: 1 is preferably obtained from the plasmid pAW 125-1, which has been deposited in the ATCC under accession No. 69886. Preferably, a DNA fragment containing the coding sequence is isolated from the pAW125-1 plasmid by PCR amplification using primer complementary to the 5' and 3' ends of SEQ ID NO: 1. Preferred primers which facilitate subsequent cloning of the amplified product are described in Example 1, below.

The present invention enables methods of producing a DNA encoding a PPase from bacteria of any species of the genus Thermus. Bacteria of the genus Thermus are thermophilic eubacteria which have been isolated from geothermal pools in various parts of the world. Representative species include *T. flavus, T. ruber, T. thermophilus, T. aquaticus, T. lacteus, T. rubens,* T. species sps 17, T. species Z05, *T. filiformis, and T. brockianus*. Various strains are available from the American Type Culture Collection, Rockville, Md.

The methods of producing a DNA encoding a PPase from bacteria of any species of the genus Thermus are based on the high level of homology present between SEQ ID NO: 1 and DNA encoding a PPase obtained from any species of the genus Thermus. The preferred method comprises (1) creating a genomic DNA library from a species of the genus Thermus, (2) transforming or transfecting an appropriate host cell with the library, (3) screening the genomic DNA library with a labeled DNA probe consisting of SEQ ID NO: 1, and (4) isolating the DNA which encodes the thermostable PPase. Genomic libraries can be screened using the colony or plaque hybridization procedure (Sambrook et al., supra) using the hybridization conditions described in the examples. One of skill in the art will understand that either strand of the double-stranded DNA that is SEQ ID NO: 1 can be used to screen the genomic library. The transformed or transfected host cell selected from step (3) in the above method can be assayed for the production of PPase activity using the assay described below.

Production of PPase is carried out using a recombinant expression clone containing SEQ ID NO: 1. The construction of the recombinant expression clone, the transformation of a host cell with the expression clone, and the culture of the transformed host cell under conditions which promote expression, can be carried out in a variety of ways using techniques of molecular biology well understood in the art. Methods for each of these steps are described in general below. Preferred methods are described in detail in the examples.

An operable expression clone is constructed by placing the coding sequence (SEQ ID NO: 1) in operable linkage with a suitable control sequences in an expression vector. The vector can be designed to replicate autonomously in the host cell or to integrate into the chromosomal DNA of the host cell. The resulting clone is used to transform a suitable host, and the transformed host is cultured under conditions suitable for expression of the coding sequence. The PPase is isolated from the medium or from the cells, although recovery and purification of the protein may not be necessary in some instances.

Construction of suitable clones containing the coding sequence and a suitable control sequence employs standard ligation and restriction techniques that are well understood in the art. In general, isolated plasmids, DNA sequences, or synthesized oligonucleotides are cleaved, modified, and religated in the form desired. Suitable restriction sites can, if not normally available, be added to the ends of the coding sequence so as to facilitate construction of an expression clone.

Site-specific DNA cleavage is performed by treating with a suitable restriction enzyme (or enzymes) under conditions that are generally understood in the art and specified by the manufacturers of commercially available restriction enzymes. See, e.g., New England Biolabs (Beverly, Mass.), Product Catalog. In general, about 1 µg of plasmid or other DNA is cleaved by one unit of enzyme in about 20 µl of buffer solution; in the examples below, an excess of restriction enzyme is generally used to ensure complete digestion of the DNA. Incubation times of about one to two hours at a temperature which is optimal for the particular enzyme are typical. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., Methods in Enzymology, 1980, 65:499–560.

Restriction-cleaved fragments with single-strand "overhanging" termini can be made blunt-ended (double-strand ends) by treating with the large fragment of E. coli DNA polymerase I (Klenow) in the presence of the four deoxynucleoside triphosphates (dNTPs) using incubation times of about 15 to 25 minutes at 20° C. to 25° C. in 50 mM Tris, pH 7.6, 50 mM NaCl, 10 mM MgCl$_2$, 10 mM DTT, and 5 to 10 µM dNTPs. The Klenow fragment fills in at 5' protruding ends, but chews back protruding 3' single strands, even though the four dNTPs are present. If desired, selective repair can be performed by supplying only one of the, or selected, dNTPs within the imitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Ligations are performed in 15–30 µl volumes under the following standard conditions and temperatures: 20 mM Tris-Cl, pH 7.5, 10 mM MgCl$_2$, 10 mM DTT, 33 µg/ml BSA, 10 mM–50 mM NaCl, and either 40 µM ATP and 0.01–0.02 (Weiss) units T4 DNA ligase at 0° C. (for ligation of fragments with complementary single stranded ends) or 1 mM ATP and 0.3–0.6 units T4 DNA ligase at 14° C. (for "blunt end" ligation). Intermolecular ligations of fragments with complementary ends are usually performed at 33–100 µg/ml total DNA concentrations (5–100 nM total ends concentration). Intermolecular blunt end ligations (usually employing a 20–30 fold molar excess of linkers, optionally) are performed at 1 µM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and pubished protocols usually accompany the commercially available BAP and CIAP enzymes. To recover the nucleic acid fragments, the preparation is extracted with phenolchloroform and ethanol precipitated to remove the phosphatase and purify the DNA. Alternatively, religation of unwanted vector fragments can be prevented by restriction enzyme digestion before or after ligation, if appropriate restriction sites are, available.

In the construction set forth below, correct ligations for plasmid construction are confirmed by first transforming a suitable host, such as E. coli strain DG101 (ATCC 47043), with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, Proc. Natl. Acad. Sci. USA 62:1159, optionally following chloramphenicol amplification (Clewell, 1972, J. Bacteriol. 110:667). Alternatively, plasmid DNA can be prepared using the "Base-Acid" extraction method at page 11 of the Bethesda Research Laboratories publication Focus, volumes5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, Proc. Natl. Acad. Sci. USA 74:5463, as further described by Messing et al., 1981, Nuc. Acids Res. 9:309, or by the method of Maxam et al., 1980, Methods in Enzymology .65:499.

The control sequences, expression vectors, and transformation methods are dependent on the type of host cell used to express the gene. Generally, procaryotic, yeast, insect; or mammalian cells are used as hosts. Procaryotic hosts are in general the most efficient and convenient for the production of recombinant proteins and are therefore preferred for the expression of PPase.

The procaryote most frequently used to express recombinant proteins is E. coli. However, microbial strains other than *E. coli* can also be used, such as bacilli, for example *Bacillus subtilis*, various species of Pseudomonas, and other bacterial strains, for recombinant expression of PPase. In such procaryotic systems, plasmid vectors that contain replication sites and control sequences derived from the host or a species compatible with the host are typically used.

For expression of constructions under control of most bacterial promoters, *E. coli* K12 strain MM294, obtained from the *E. coli* Genetic Stock Center under GCSC #6135, can be used as the host. For expression vectors with the $P_LN_{RBS}$ or $P_LT_{7RBS}$ control sequence, *E. coli* K12 strain MC1000 lambda lysogen, $\lambda N_7N_{53}CI857$ SusP$_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassett is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six bp 3' of the $N_{RBS}$ sequence. Also useful is the phosphatase A (phoA) system described by Chang et al., in European Patent Publication No. 196,864, published Oct. 8, 1986. However, any available promoter system compatible with procaryotes can be used to construct a expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979; *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme Reg.* 7:149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast expression vectors.

The PPase coding sequence can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986), Setlow et al., eds., Plenum Publishing, Vol. 8, pp. 277-297). Insect cell-based expression can be accomplished in *Spodoptera frugipeida*. These systems are also successful in producing recombinant enzymes.

Depending on the host cell used, transformation is done using standard techniques appropriate to such cells. The calcium treatment employing calcium chloride, as described by Cohen, 1972, *Proc. Natl. Acad. Sci. USA* 69:2110 is used for procaryotes or other cells that contain substantial cell wall barriers. Infection with *Agrobacterium tumefaciens* (Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946, and Hsiao et al., 1979, *Proc. Natl. Acad. Sci. USA* 76:3829.

It may be desirable to modify the sequence of the DNA encoding the PPase from a species of the genus Thermus to, for example, provide a sequence more compatible with the codon usage of the host cell without modifying the amino acid sequence of the encoded protein. Such modifications to the initial 5–6 codons may improve expression efficiency. DNA sequences which have been modified to improve expression efficiency, but which encode the same amino acid sequence, are considered to be equivalent and encompassed by the present invention. A variety of site-specific primer-directed mutagenesis methods are available and well-known in the art. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in a single-stranded vector, such as pBSM 13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

Once the PPase has been expressed in a recombinant host cell, purification of the protein may be desired. A variety of purification procedures can be used to purify the recombinant thermostable PPase of the invention. In a preferred method, the expression of PPase is carried out in *E. coli*, which is a mesophilic bacterial host cell. Because *E. coli* host proteins are heat-sensitive, the recombinant thermostable PPase can be substantially enriched by heat inactivating the crude lysate. This step is done in the presence of a sufficient amount of salt (typically 0.3M ammonium sulfate) to ensure to reduce ionic interactions of PPase with other cell lysate proteins.

In addition, the presence of ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture containing recombinant PPase is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used which contains, for example, 1.0M ammonium sulfate. The column is equilibrated in a buffer containing 1.0M ammonium sulfate, 25 mM Tris (pH 7.5), 1.0 mM EDTA, and 1.0 mM DTT, and the sample is applied to the column. The column is washed with buffer. The enzyme may then be eluted with solvents which attenuate hydrophobic interactions, such as decreasing salt gradients, or increasing gradients or addition of ethylene or propylene glycol, or urea. For example, the enzyme may be eluted from the column with 4 column volumes of TE buffer (25 mM Tris (pH 7.5), 1.0 mM EDTA, and 1.0 mM DTT).

Activity of the purified PPase is assayed as follows. The purified enzyme is used in the hydrolysis of inorganic pyrophosphate (PPi) with subsequent release of two orthophosphates, and resulting amount of orthophosphate is measured. The hydrolysis reaction is carried out in a 0.5 ml reaction volume containing 0.4M NaPPi, 50 mM Tris-HCl (pH 9.0), and 1.5 mM $MgCl_2$ or 0.75 mM $MnCl_2$. Following incubation at 55° C. for 10 minutes, the hydrolysis is stopped by adding an equal volume of 8% TCA, to a final volume of 1.0 ml. The inorganic monophosphate released is assayed using the Sigma Diagnostics Phosphorous reagents (Sigma, St. Louis, Mo.). An ammonium molybdate solution (200 µl) and a Fiske and Subbarow reducer (50 µl of 1-amino-2-napthol-4-sulfonic acid, 0.8%, sodium sulfite, and sodium bisulfite) are added to the reaction mixture, which results in the formation of a phosphomolybdenum blue complex. The concentration of phosphate is proportional to the optical density $[A_{660}]$ of the reaction mixture. In this assay, an optical density of 1.1 corresponds to a complete hydrolysis of the NaPPi.

The thermostable enzyme of this invention may be used for any purpose in which a thermostable protein possessing pyrophosphatase enzyme activity is necessary or desired.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE 1

Construction of a Pyrophosphatase Expression System

A DNA fragment containing the entire PPase coding sequence is isolated from pasmid pAW125-1 by PCR amplification using the two oligonucleotide primers, P1 (SEQ ID NO: 2) and P2 (SEQ ID NO: 3). Primer P1 (SEQ ID NO: 2) hybridizes to the 5' end of the Tth PPase gene at amino acid position 1 to 6, and introduces an NcoI restriction site into the amplified product. Primer P2 (SEQ ID NO: 3) hybridizes to the 3' end of the Tth PPase gene at amino acid position 171–176, and changes the TAG stop codon to TAA and introduces a BamHI restriction site. The use of a TAA stop codon is preferred for translation termination in many *E. coli*. host strains. The sequences of the primers used in the amplification are shown below. The region of the primer which hybridizes to SEQ ID NO: 1 is shown underlined; the restriction sites are shown in bold.

Primer Sequences

P1 (SEQ ID NO: 2) 5'-CATGCCATGGCGAACCTGAAGAGC

P2 (SEQ ID NO: 3) 5'-GCCGGATCCTTAGCCCTTGTAGCGGGC

Amplification is carried out using the. GeneAmp PCR Reagent Kit with AmpliTaq® DNA Polymerase (Perkin Elmer, Norwalk, Conn.). The resulting 543 bp PCR product is digested with NcoI and BamHi and ligated with an expression vector pDG182, which had been digested with NcoI and BamHI, using standard techniques. Plasmid pDG182 is described in U.S. Pat. No. 5,420,029, incorporated herein by reference. Plasmid pDG 182 is a derivative of plasmid pDG160. Plasmid pDG160 and the scheme for constructing vectors such as to pDG182 are described in copending U.S. Ser. No. 08/384,490, incorporated herein by reference.

The resulting expression plasmid (5989 bp) is under the control of the bacteriophage lambda $P_L$ promoter, the T7 gene 10 ribosome-binding site and a Positive Retroregulatory Element (PRE, transcription terminator) from the *Bacillus thuringiensis* delta-toxin gene. The plasmid also carries a mutated RNA II gene which renders the plasmid temperature sensitive for copy number and an ampicillin resistance gene.

The expression plasmid is transformed into DG116 host cells (ATCC 53606), resulting in a PPase expression system. Because, prior to cloning, the PPase DNA sequence is amplified by PCR, which can introduce random errors in the sequence, isolates should be sequenced to ensure the DNA sequence fidelity in the expression plasmid.

EXAMPLE 2

Expression of Pryophosphatase

This example describes the expression of thermostable PPase using an expression system constructed essentially as described in Example 1, above.

Growth and expression were carried out in 20 ml shake flasks containing tryptone (20 g/l), yeast extract (10 g/l), NaCl (10 g/l), glucose (10 g/l), ampicillin (50 mg/l), and thiamine (10 mg/l). The shake flasks were inoculated with a 1% volume of a fresh overnight culture that had been innoculated with a single colony of the transformed DG116 cells from an agar plate (a frozen glycerol culture can be used).

Cultures were grown at 30° C. to an optical density $[A_{600}]$ of 0.5 to 0.7. To induce expression of the PPase gene, the temperature was raised from 30° C. to 37° C. or 39° C. Following incubation for 18 hours, the cells were harvested.

Crude cell extracts were heated at 75° C. for 15 min, chilled on ice, and centrifuged at 12,000×G for 5 minutes. The supernatants were analyzed by SDS-PAGE. Based on the predicted sequence, the predicted molecular weight of the recombinant PPase is 19 kilodaltons (kDa) with an isoelectric point of 4.89 and extinction coefficient of 20400. However, the PPase was observed to migrate as if it were a 24 kDa polypeptide using the SDS-PAGE system described above. A high level of PPase expression was observed from both the 37° C. and 39° C. inductions.

EXAMPLE 3

Purification of Recombinant Pyrophosphatase

This example describes the large-scale expression and purification of recombinant PPase. Large scale growth and expression were carried out in a 10 l fermentor. The expression system used was essentially as described in example 1.

A. Expression

Initial growth was carried out in a 250 ml Klett flask containing 95 ml of 1× Bonner Vogel minimal medium (9.6 mM citric acid, 57 mM $KH_2PO_4$, 16.8 mM $NaNH_4HPO_4$, 0.8 mM $MgSO_4$) supplemented with 0.4 ml 50% glucose, 0.1 ml 1% thiamine, 1.25 ml 20% casamino acid, 1.0 ml 1% ampicillin, and 1.0 ml 1% methicillin. The Klett flask was innoculated with the 1.0 ml of expression system cell culture (a colony from an agar plate or a frozen glycerol culture can be used). The flask was incubated at 30° C. until an optical density of 216 Klett units was obtained.

The culture medium was prepared in a 10 l fermentor as follows. The following reagents were added to 6 l of $dH_2O$: 40.00 ml trace mineral solution (0.4 mM $FeCl_3$, 0.04 mM $ZnCl_2$, 0.03 mM $CoCl_2$, 0.03 mM $CuCl_2$, and 0.03 mM $H_3BO_3$), 11.76 g sodium citrate, 34.0 g $KH_2PO_4$, and 37.0 g $(NH_4)_2SO_4$. The pH was adjusted to 6.5 using 5N NaOH, the mixture autoclaved, and the volume brought up to 8.0 l with $dH_2O$. The following sterile components were added: 80 ml 0.5M $MgSO_4$, 150 ml 50% glucose, 20 ml 1% thiamine, 125 ml 20% casamino acid, 100 ml 1% ampicillin, and 100 ml 1% methicillin. During the fermentation, glucose was continually added, and the pH was controlled by adding $NH_4OH$. Foaming can be controlled by the addition of propylene glycol as necessary, as an antifoaming agent. Dissolved oxygen concentration was maintained at 40%.

Thirteen ml of the inital culture was inoculated into the fermentor culture medium. Following inoculation of the 10 l fermentor, as described above, the culture was grown at 30° C. until an optical density $[A_{600}]$ of 17.8 was obtained. The growth temperature was shifted to 38° C. to induce the synthesis of PPase. The temperature shift increases the copy number of the expression plasmid and simultaneously derepresses the lambda $P_L$ promoter controlling transcription of the modified PPase gene through inactivation of the temperature-sensitive cI repressor encoded by the defective prophage lysogen in the host.

Samples were taken after the cells were grown for 6 hours and 17 hours, respectively, and the cells were harvested by centrifugation. The cells were stored in 250 ml centfuge bottles at −70° C. The volume and yield of the samples are shown below.

| Yield of Expression System Cells | | | |
|---|---|---|---|
| Time of Sample | Volume | Optical Density $[A_{680}]$ | Cells Weight |
| 6 hours | 1.5 l | 51.9 | 106 g |
| 17 hours | 8.5 l | 46.0 | 505 g |

B. Purification

Forty g of cells were thawed in 1 volume of 2× lysis buffer (100 mM Tris-HCl pH7.5, 30 mM EDTA pH8.0 and 2 mM DTT), and protease inhibitors were added (Pefabloc to 4 mM, Leupeptin to 2 µg/ml, and TLCK to 0.4 mM [Sigma, St. Louis, Mo.]). The cells were lysed in an Aminco french pressure cell at 20K psi. The lysate was diluted with 1× lysis buffer and protease inhibitors to 5× wet weight cell mass, and sonicated at 50% duty cycle for 3 minutes to reduce the viscosity. The sonicate was heated at 85° C. for 15 minutes. The heat-treated supernatant was chilled rapidly to 0° C., and the *E. coli* cell membranes and denatured proteins were removed following centrifugation at 35,000×G for 20 minutes. Polymin P (polyethyleneimine, PEI) was added slowly to the supernatant to 0.25% (w/v) to precipitate the PPase. The PPase was resuspended (using a homogenizer to break the precipitated pellet) in the presence of 0.2M ammonium sulfate. The suspension was centrifuged at 30,000×G for 15 min, and the supernatant containing the PPase was saved.

The supernatant was adjusted to 1.0M ammonium sulfate and applied to a phenyl sepharose Column (2.2×18 cm) that had been equilibrated in 1.0M ammonium sulfate, 25 mM Tris-HCl pH 7.5, 1.0 mM EDTA, and 1.0 mM DTT. The column was washed with 3 column volumes of the same buffer. The PPase was then eluted from the column with 4 column volumes of TE buffer (25 mM Tris pH7.5, 1.0 mM EDTA, and 1.0 mM DTT), and fractions containing PPase analyzed by SDS-PAGE were pooled.

The pool was diluted with TE buffer to the ionic strength equal to 40 mM KCl, and loaded onto a DEAE-sepharose column (3.2×17.5 cm) that had been equilibrated in 40 mM KCl+TE buffer. The column was washed with 3 column volumes of the same buffer and eluted with a linear gradient of 40–300 mM KCl in TE buffer. The peak fractions containing the PPase were pooled and diafiltered into 2.5× storage buffer (20 mM Tris-HCl pH 8.0, 100 mM KCl, 1.0 mM DTT, and 0.1 mM EDTA), combined with 1.5 volumes of sterile 80% (w/v) glycerol, and stored at −20° C.

The recombinant PPase obtained was assayed for PPase activity essentially as described above. A high level of activity was observed over a broad range of pH (about 8.0 to 10.0) and temperatures (about 50°–90° C.). The temperature optimum was about 75° C. in the presence of $MgCl_2$ and about 85° C. in the presence of $MnCl_2$. Thermostability of the enzyme was measured by incubating the enzyme at 90° C. or 95° C. and then measuring the residual enzyme activity as described above. The half-life of the recombinant PPase activity (incubation time resulting in 50% loss of activity) was 30 minutes when incubated at 90° C. and 10 minutes when incubated at 95° C.

EXAMPLE 4

Cloning of the Pyrophosphatase Gene From Other Themus Species

This example describes the isloation of a PPase gene from other species of the genus Thermus. The method involves screening a genomic DNA library using a radiolabeled probe consisting of SEQ ID NO: 1.

Bacteria from a species of the genus Thermus are grown using standard techniques, such as those described in U.S. Pat. Nos. 4,889,818 and 5,405,774, both incorporated herein by reference. DNA is purified by the method described in Lawyer et al., 1989, *J. Biological Chemistry* 264(11):6427–6437, which is incorporated herein by reference.

In order to determine which restriction enzyme is most useful in preparation of a genomic library, genomic DNA (0.5 μg) from the Thermus species is digested, in separate experiments, with HindIII, EcoRI, BamHI, KpnI, BglII, SacI, or other enzymes. The digested DNA fragments are separated by gel electrophoresis through an 0.8% agarose gel. The DNA fragments in the gel are denatured in 1.5M NaCl and 0.5M NaOH solution for 30 minutes, neutralized in a solution of 1M Tris-HCl, pH 8.0 and 1.5M NaCl for 30 minutes, and then transferred to a Biodyne nylon membrane (Pall Biosupport, East Hills, N.Y.) using 20× SSPE (3.6M NaCl, 200 mM $NaPO_4$ pH 7.4, 20 mM EDTA pH 7.4).

The DNA attached to the membrane is then hybridized to a $^{32}$P-labeled probe consisting of SEQ ID NO: 1. Labeling of the probe is carried out using standard methods well known in the art (e.g., see. Sambrook et al., supra; or using a random primer kit (New England Biolabs, Inc. Beverly, Mass.)). Membranes are prehybridized in a solution containing 6× SSPE, 5× Denhardt's reagent, 0.5% SDS, 100 μg/ml denatured, sheared salmon sperm DNA. Hybridization is carried out at 50°–55° C. in a hybridization solution containing 6× SSPE, 2× Denhardt's reagent, 0.5% SDS, 100 μg/ml denatured, sheared salmon sperm DNA, and $10^6$ cpm $[^{32}P]$-labeled probe. The membrane is washed in 6× SSPE, 0.1% SDS for 5 minutes at room temperature, followed by a wash in 2× SSPE, 0.1% SDS for 15 minutes at 55° C. Restriction enzymes which result in a single major band (preferably, between 0.75 and 3 kb), which indicates that the entire gene is contained on a single fragement, are prefered for use in creating a genomic DNA library.

A genomic DNA library is constructed as follows. About 25 μg of Thermus DNA is digested with the restriction enzyme selected as described above and size-fractionated by gel electrophoresis. Between 10 and 50 ng of fragments within the size range determined by gel electrophoresis and Southern blotting as described above are used for cloning into a suitable cloning vector. The cloning vector is chosen to be compatible with the restriction enzyme used. For example, genomic DNA fragments digested with BamHI or BglII can be cloned into the BamHI site of pUC19 vector (Clontech, Palo Alto, Calif.). The pUC19 plasmid vector has the lac promoter upstream from the BamHI cloning site. The promoter can induce heterologous expression of cloned open reading frames lacking promoter sequences. The recombinant plasmids are transformed into a suitable host, such as *E. coli* SURE cells (Strategene, La Jolla, Calif.).

A $[^{32}P]$-labeled probe consisting of SEQ ID NO: 1 is used to screen the genomic DNA library. Either strand of the double-stranded DNA that is SEQ ID NO: 1 can be labeled and used as a probe to screen the genomic library. Genomic libraries can be screened using the colony hybridization procedure (Sambrook et al., supra). The genomic library is hybridized with the labeled probe under the same conditions as used above. Specifically, membranes are prehybridized in a solution containing 6× SSPE, 5× Denhardt's reagent, 0.5% SDS, 100 μg/ml denatured, sheared salmon sperm DNA. Hybridization is carried out at 50°–55° C. in a hybridization solution containing 6× SSPE; 2× Denhardt's reagent, 0.5% SDS, 100 μg/ml denatured, sheared salmon sperm DNA, and $10^6$ cpm $^{32}$P-labeled probe. The membrane is washed in 6× SSPE, 0.1% SDS for 5 minutes at room temperature, followed by a stringent wash in 2× SSPE, 0.1% SDS for 15 minutes at 55° C. Positive colonies are selected and can be purified and replated until 90–100% of the colonies are positive for each isolate.

Restriction analysis is performed on the plasmid DNAs isolated from these clones to determine the size and orientation of insert fragments relative to the vector. DNA sequence analysis is performed using methods well-known in the art. The "universal" forward and reverse sequencing primers, Nos. 1212 and 1233, respectively, purchased from New England BioLabs, Beverly, Mass., are used to obtain preliminary DNA sequences. From the preliminary DNA sequence, further sequencing primers are designed to obtain DNA sequence of more internal regions of the cloned insert. DNA sequence analysis should be performed for both strands.

| Deposits | |
|---|---|
| The following deposit was made on August 11, 1995 | |
| Strain Deposit Date | ATCC No. |
| pAW125-1 | 69886 |

This deposit was made under the provisions of the Budapest Treaty on the International Recognition of the Deposit of Microorganisms for the Purposes of Patent Procedure and the Regulations thereunder (Budapest Treaty). This assures maintenance of a viable culture for 30 years from date of deposit. The organism will be made available by ATCC under the terms of the Budapest Treaty, and subject to an agreement between Applicants and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638). The assignee of the present application agrees that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

We claim:

1. An isolated DNA consisting of SEQ ID NO: 1.
2. A vector comprising the isolated DNA of claim 1.
3. The vector of claim 2 that is pAW125-1.
4. An expression vector comprising the isolated DNA of claim 1.
5. A host cell transformed with the expression vector of claim 4.
6. A method for preparing a thermostable pyrophosphatase, comprising:
   (a) culturing a host cell of claim 5 under conditions which promote the expression of thermostable pyrophosphatase; and
   (b) isolating thermostable pyrophosphatase from said host cell.
7. A method for isolating a target DNA fragment comprising a DNA coding for a thermostable pyrophosphatase from a bacterium of the genus Thermus, comprising:
   (a) forming a genomic library from said bacterium;
   (b) transforming or transfecting an appropriate host cell with the library of step (a);
   (c) contacting DNA from a transformed or transfected host cell of step
   (b) with a DNA probe consisting of SEQ ID NO: 1 under hybridization conditions consisting of the following:
      (1) hybridization: 6× SSPE, 2× Denhardt's reagent, 0.5% SDS, and 100 µg/ml denatured, sheared salmon sperm DNA at 50°–55° C.; and
      (2) wash: 2× SSPE, 0.1% SDS for 15 minutes at 55° C.;
   (d) isolating DNA which encodes a thermostable pyrophosphatase.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 528 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGGCGAACC TGAAGAGCCT TCCCGTGGGC GACAAGGCGC CCGAGGTGGT CCACATGGTC    60
ATTGAGGTCC CCCGCGGCTC GGGCAACAAG TACGAGTACG ACCCGGACCT CGGGGCGATC   120
AAGCTGGACC GGGTCCTGCC GGGAGCCCAG TTCTACCCCG GGGACTACGG CTTCATCCCC   180
TCCACCCTGG CCGAGGACGG GGACCCCTTG GACGGCCTCG TCCTCTCCAC CTACCCCCTC   240
CTCCCCGGGG TGGTGGTGGA GGTCCGGGTG GTGGGCCTCC TCCTCATGGA GGACGAGAAG   300
GGCGGGGATG CCAAGGTCAT CGGGGTGGTG GCCGAGGACC AGCGCCTGGA CCACATCCAG   360
GACATCGGGG ACGTCCCCGA GGGCGTGAAG CAAGAGATCC AGCACTTCTT TGAGACCTAC   420
AAGGCCCTCG AGGCCAAGAA GGGGAAGTGG GTCAAGGTCA CGGGCTGGCG GGACCGGAAG   480
GCGGCCTTGG AGGAGGTCCG GGCCTGCATC GCCCGCTACA AGGGCTAG              528
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CATGCCATGG CGAACCTGAA GAGC                                           24
```

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCCGGATCCT TAGCCCTTGT AGCGGGC                                        27
```